(12) United States Patent
Ralph et al.

(10) Patent No.: US 8,128,670 B2
(45) Date of Patent: Mar. 6, 2012

(54) SURGICAL EXPANSION FASTENERS

(75) Inventors: James D. Ralph, Bethlehem, PA (US);
Stephen L. Tatar, Montville, NJ (US);
Thomas N. Troxell, Pottstown, PA (US)

(73) Assignee: BioDynamics LLC, Englewood, NJ (US)

( * ) Notice: Subject to any disclaimer, the term of this patent is extended or adjusted under 35 U.S.C. 154(b) by 1327 days.

(21) Appl. No.: 11/107,610

(22) Filed: Apr. 15, 2005

(65) Prior Publication Data
US 2006/0235410 A1  Oct. 19, 2006

(51) Int. Cl.
*A61B 17/58* (2006.01)
(52) U.S. Cl. ......... 606/313; 606/323; 606/326; 606/301
(58) Field of Classification Search ............ 606/63, 606/66, 71–73, 62, 68, 300–319, 323, 326, 606/327; 411/14.5, 15, 16, 18, 22, 25, 26, 411/29, 30, 32, 35, 43, 44, 45, 53, 54.1, 57.1, 411/60.2, 69, 72, 73, 80.1, 80.2, 80.6
See application file for complete search history.

(56) References Cited

U.S. PATENT DOCUMENTS

| | | |
|---|---|---|
| 3,385,156 A | 5/1968 | Polos |
| 3,487,746 A | 1/1970 | Kapnek |
| 3,651,934 A | 3/1972 | Roberts et al. |
| 3,888,156 A | 6/1975 | Fima |
| 4,143,581 A | 3/1979 | Smith |
| 4,152,968 A | 5/1979 | Lassine |
| 4,197,781 A | 4/1980 | Giannuzzi |
| 4,233,881 A | 11/1980 | Carrier |
| 4,236,512 A | 12/1980 | Aginsky |
| 4,248,458 A | 2/1981 | Brody |
| 4,275,717 A | 6/1981 | Bolesky |
| 4,285,225 A | 8/1981 | Snell |
| 4,307,598 A | 12/1981 | Andrich |
| 4,388,031 A | 6/1983 | Rodgers |
| 4,415,299 A | 11/1983 | Smith et al. |
| 4,453,539 A | 6/1984 | Raftopoulos et al. |
| 4,590,930 A | 5/1986 | Kurth et al. |
| 4,632,101 A | 12/1986 | Freedland |
| 4,657,456 A | 4/1987 | Anquetin |
| 4,704,057 A | 11/1987 | McSherry |
| 4,716,893 A * | 1/1988 | Fischer et al. ............... 606/66 |
| 4,721,103 A | 1/1988 | Freedland |
| 4,752,170 A | 6/1988 | McSherry et al. |
| 4,764,065 A | 8/1988 | Johnson |
| 4,828,439 A | 5/1989 | Giannuzzi |

(Continued)

OTHER PUBLICATIONS

Kris Hundley, "Believing in biotech", *St. Petersburg Times*, published Nov. 3, 2003.

(Continued)

*Primary Examiner* — Eduardo C Robert
*Assistant Examiner* — Tara Carter
(74) *Attorney, Agent, or Firm* — Lowenstein Sandler PC

(57) ABSTRACT

A biocompatible surgical fastener, comprising a sleeve and a screw or a pin, which expands when it is implanted in a patient. The sleeve is first implanted in a pre-drilled hole in the operating area of a patient, usually in a bone, cartilage or a bone and cartilage. When a screw or a pin is installed in the sleeve, the sleeve is caused to expand thereby stabilizing the fastener in the operating area. In many embodiments the screw or pin can be removed and reinserted without disturbing the tissue in the operating area. The surgical fastener can be used to repair tissue or to secure other implant devices in a patient.

28 Claims, 13 Drawing Sheets

U.S. PATENT DOCUMENTS

| | | | |
|---|---|---|---|
| 4,862,883 A | | 9/1989 | Freeland |
| 5,057,103 A | | 10/1991 | Davis |
| 5,098,433 A | | 3/1992 | Freedland |
| 5,203,864 A | | 4/1993 | Phillips |
| 5,236,438 A | | 8/1993 | Wilk |
| 5,244,324 A | | 9/1993 | Smith |
| 5,268,001 A | * | 12/1993 | Nicholson et al. ............. 606/72 |
| 5,439,381 A | | 8/1995 | Cohen |
| 5,462,552 A | | 10/1995 | Kiester |
| 5,470,230 A | | 11/1995 | Daftary et al. |
| 5,509,765 A | | 4/1996 | Albin |
| 5,601,558 A | | 2/1997 | Torrie et al. |
| 5,690,454 A | | 11/1997 | Smith |
| 5,720,753 A | * | 2/1998 | Sander et al. ............. 606/104 |
| 5,849,004 A | | 12/1998 | Bramlet |
| 5,911,721 A | | 6/1999 | Nicholson et al. |
| 5,935,169 A | * | 8/1999 | Chan ..................... 623/23.48 |
| 5,957,953 A | * | 9/1999 | DiPoto et al. ............. 606/232 |
| 5,968,044 A | | 10/1999 | Nicholson et al. |
| 5,976,139 A | | 11/1999 | Bramlet |
| 5,980,524 A | | 11/1999 | Justin et al. |
| 5,980,559 A | * | 11/1999 | Bonutti ..................... 606/232 |
| 6,062,785 A | | 5/2000 | McDermott |
| 6,077,265 A | | 6/2000 | Chemello |
| 6,146,384 A | | 11/2000 | Lee et al. |
| 6,183,474 B1 | | 2/2001 | Bramlet et al. |
| 6,241,732 B1 | * | 6/2001 | Overaker et al. ............. 606/72 |
| 6,270,304 B1 | | 8/2001 | Freedland |
| 6,287,310 B1 | | 9/2001 | Fox |
| 6,290,701 B1 | | 9/2001 | Enayati |
| 6,406,479 B1 | | 6/2002 | Justin et al. |
| 6,540,751 B2 | | 4/2003 | Enayati |
| 6,551,282 B1 | | 4/2003 | Exline et al. |
| 6,554,553 B2 | | 4/2003 | Freedland |
| 6,583,232 B1 | | 6/2003 | Brown |
| 6,613,053 B1 | | 9/2003 | Collins et al. |
| 6,695,844 B2 | | 2/2004 | Bramlet et al. |
| 6,755,831 B2 | | 6/2004 | Putnam et al. |
| 6,942,666 B2 | | 9/2005 | Overaker et al. |
| 2001/0005475 A1 | * | 6/2001 | Frigg ..................... 411/501 |
| 2002/0161369 A1 | | 10/2002 | Bramlet et al. |
| 2004/0092937 A1 | | 5/2004 | Criscuolo et al. |
| 2004/0153125 A1 | | 8/2004 | Roby |
| 2004/0208721 A1 | | 10/2004 | Kuenzel |
| 2006/0074421 A1 | | 4/2006 | Bickley et al. |
| 2006/0206208 A1 | | 9/2006 | Michelson |

OTHER PUBLICATIONS

Piltz, S. MD, Steinbauer, T., Meyer, L. MD, Plitz, W. MD, Andress, H. J MD, Lob, G. MD, "Bioabsorbable Expansion Bolt Fixation in Anterior Cruciate Ligament Reconstruction", *Clinical Orthopaedics & Related Research*, (418):225-230, Jan. 2004, published by Lippincott Williams & Wilkins, copyright © 2005, Lippincott Williams & Wilkins.

Talon Technology™ information, taken from Orthopedic Designs, Inc. website (www.orthopedicdesigns.com) on Feb. 28, 2005.

Technical Information on the Resofix® Absorbable Expansion Bolt, taken from MD Supply Switzerland website (www.md-supply.ch) on Mar. 7, 2005.

International Search Report, May 28, 2008.

* cited by examiner

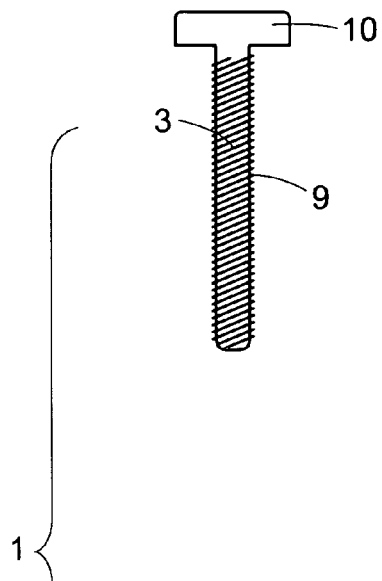
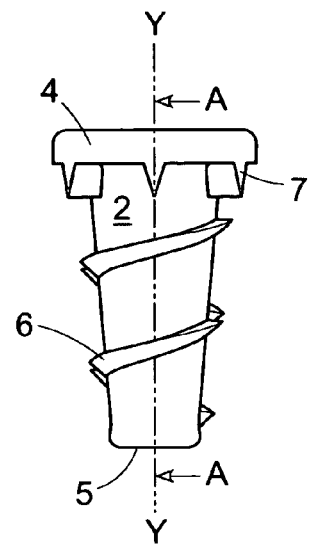
FIG. 1B
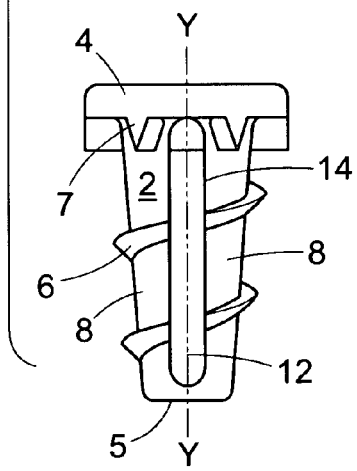
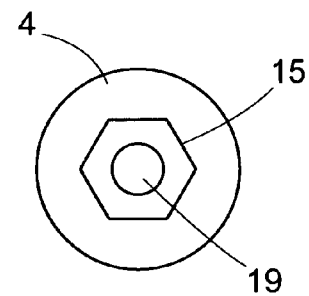
FIG. 1A  FIG. 1C

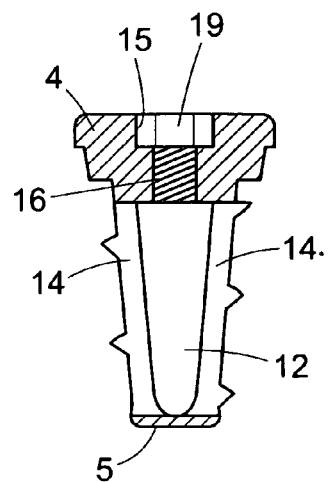
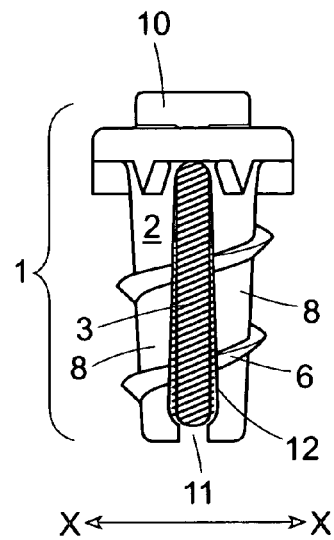
FIG. 1D  FIG. 2
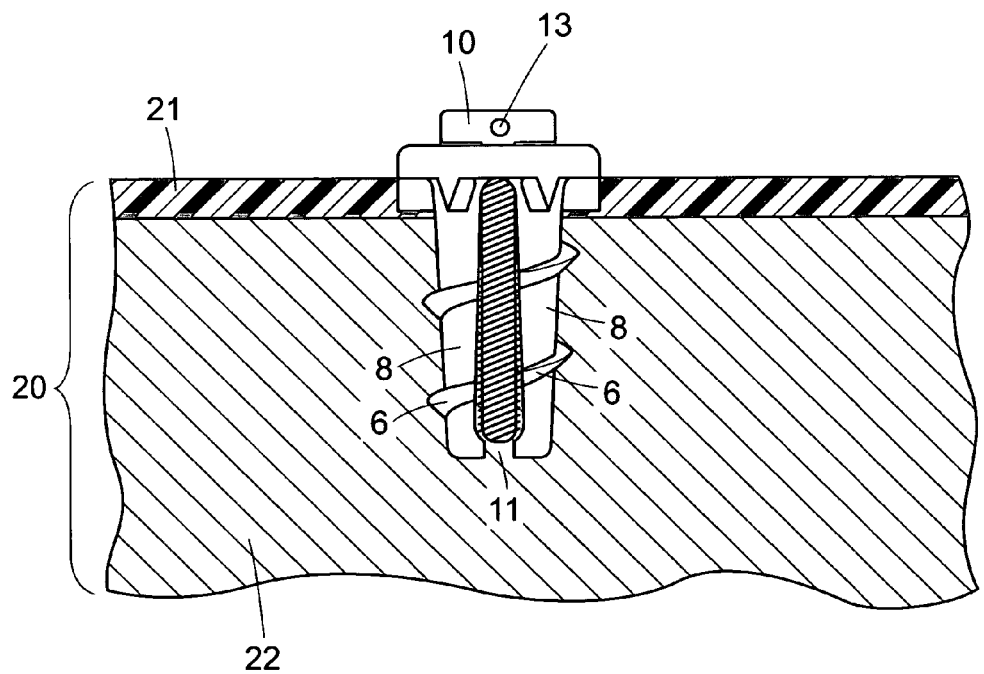
FIG. 3

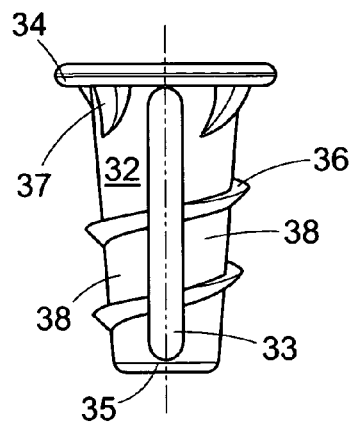
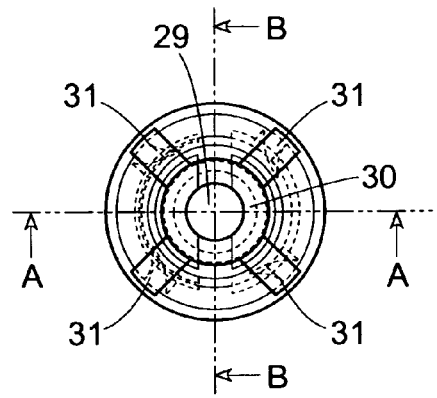
FIG. 4A  FIG. 4B
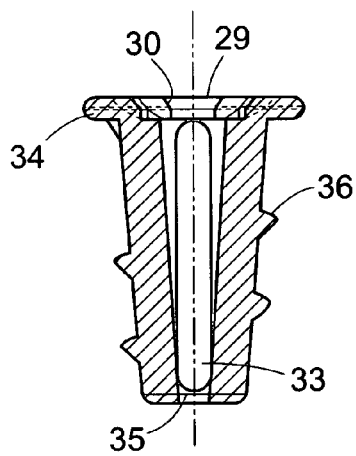
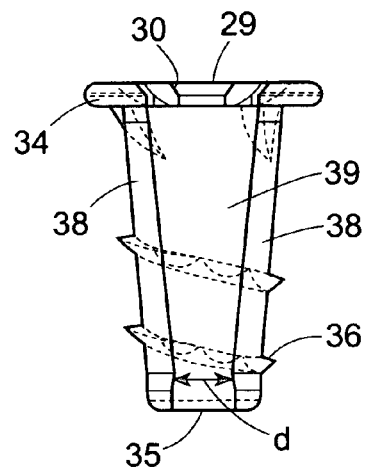
FIG. 4C  FIG. 4D
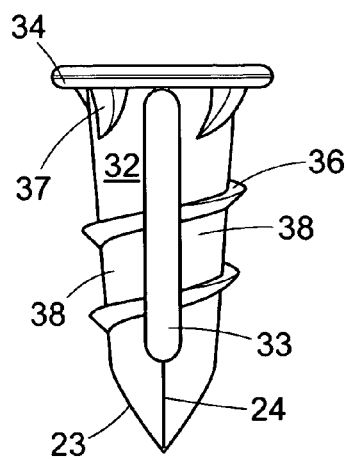
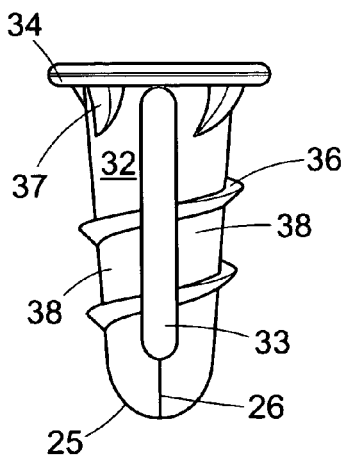
FIG. 4E  FIG. 4F

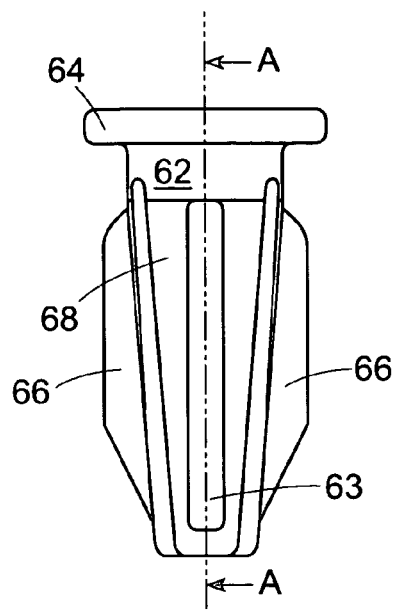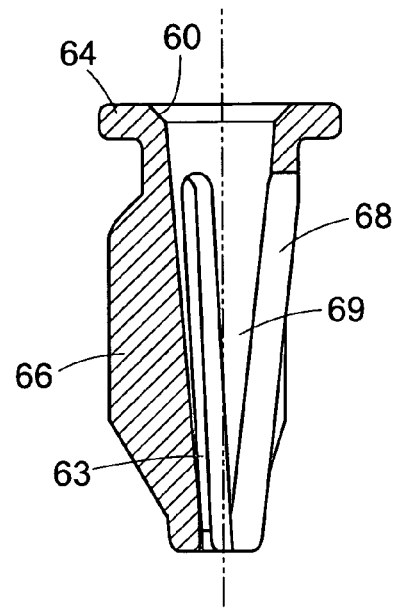
FIG. 7A
FIG. 7C
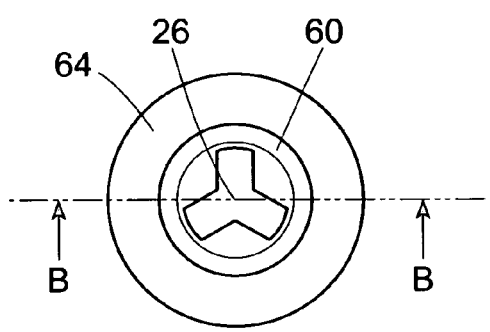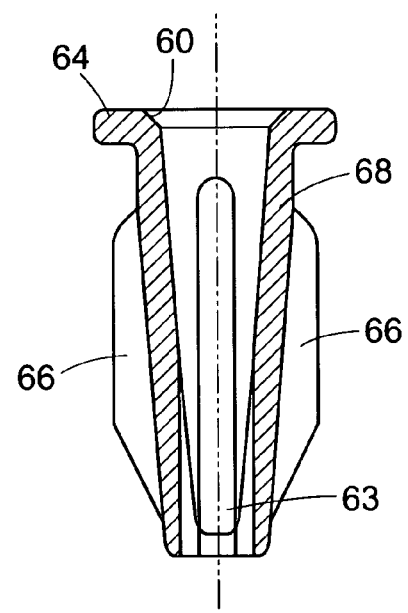
FIG. 7B
FIG. 7D

SURGICAL EXPANSION FASTENERS

BACKGROUND OF THE INVENTION

1. Field of the Invention

The present invention has to do with surgical fasteners which are implanted in the body. In particular, the invention has to do with improved surgical fasteners which expand when they are implanted in a patient. The expansion stabilizes the fastener in the patient.

2. The Related Art

Expansion fasteners such as the Molly® expansion bolt sold by The Black & Decker Corporation are known in the fastener art. Applicants have now discovered that fastener products employing similar principles can be modified in new ways for use as surgical implants.

Bone, except in the skull, has an outside cortical shell which is hard and strong with an average thickness from about 0.05-0.4 millimeters ("mm"). The portion of the bone under the cortical shell is cancellous and is a much softer material. This characteristic of bone structure creates problems in surgery. Conventional surgical screws, for example, can loosen and become unstable, for example, they may rotate over time and pull out requiring re-surgery. They can also break or become infected and have to be removed. They may be overtightened causing the bone to be stripped out or the patient may have weak bone tissue or bones weakened by disease such as osteoporosis so that the bones are not strong enough to hold the screw. These problems and many others are solved by the fasteners of the present invention.

SUMMARY OF THE INVENTION

The invention has to do with surgical fasteners which expand when they are implanted in a patient. Each fastener is comprised of a sleeve in combination with a screw or a pin. The sleeve is designed to receive the screw or pin. And when the screw or pin is inserted into the sleeve, at least a portion of the sleeve expands. During surgery, the sleeve, with or without a partially inserted screw or pin, is first implanted in a pre-drilled hole in the operating area, usually a bone and sometimes also the cartilage, of the patient. Then the screw or pin is sufficiently inserted into the sleeve to cause the sleeve to expand. The expansion stabilizes the fastener in the patient. In many embodiments, the screw or pin can be removed and reinserted without disturbing the bone tissue.

The surgical applications for use of the fasteners of the invention are numerous. They are useful in any application where a surgeon might need a means to repair a bone, attach cartilage or a tendon to a bone, anchor another medical implant device, and the like. For example, the fasteners can be inserted through the top tibial trays, can be used to hold down trauma plates, artificial joints, other plates and mesh materials, acetabulum cups, external halos and the like.

BRIEF DESCRIPTION OF THE DRAWINGS

The drawings are intended to be illustrative, are not drawn to scale and are not intended to limit the scope of the claims to the embodiments depicted.

FIGS. I-A and I-B are elevation views of a screw/threaded-type fastener of the invention before the screw is inserted in the threaded sleeve.

Figure 5A:
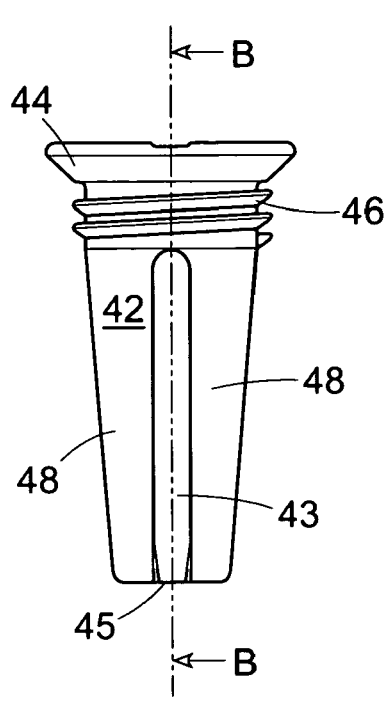
Figure 5B:
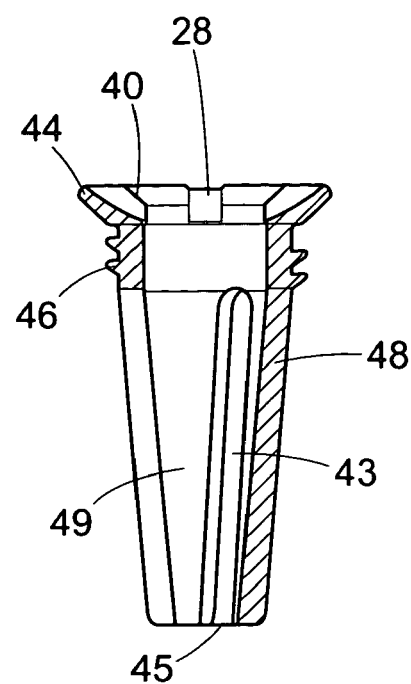
Figure 5C:
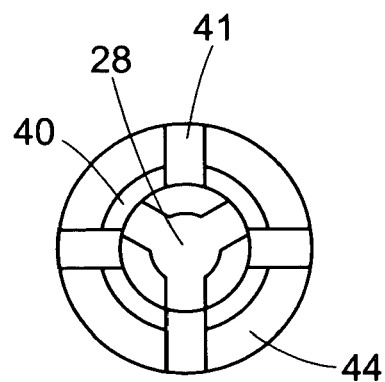
Figure 6A:
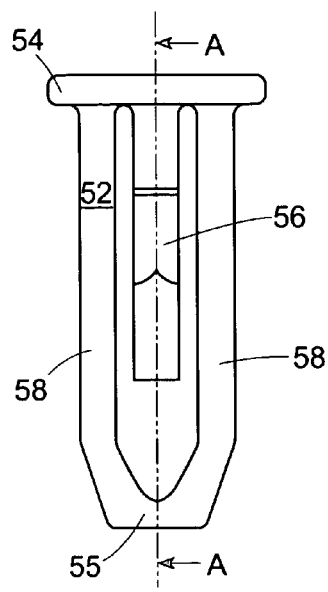
Figure 6B:
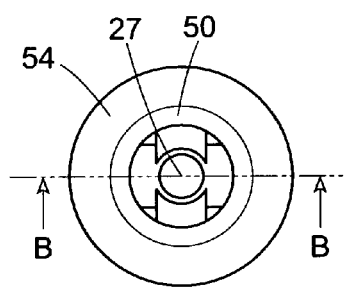
Figure 6C:
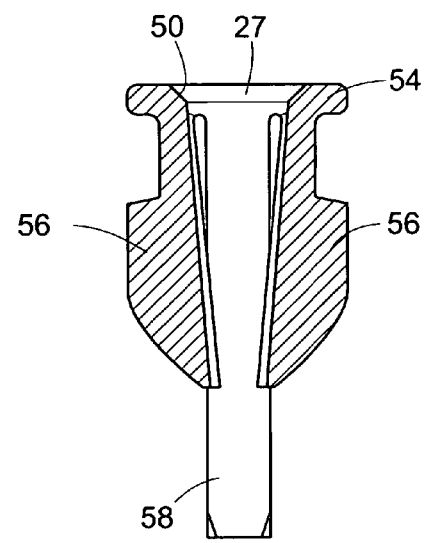
Figure 6D:
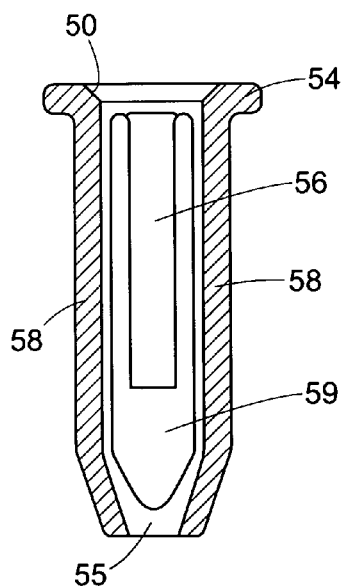
Figure 6E:
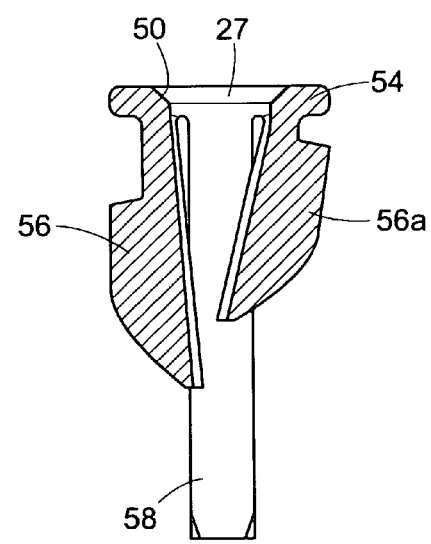
Figure 8A:
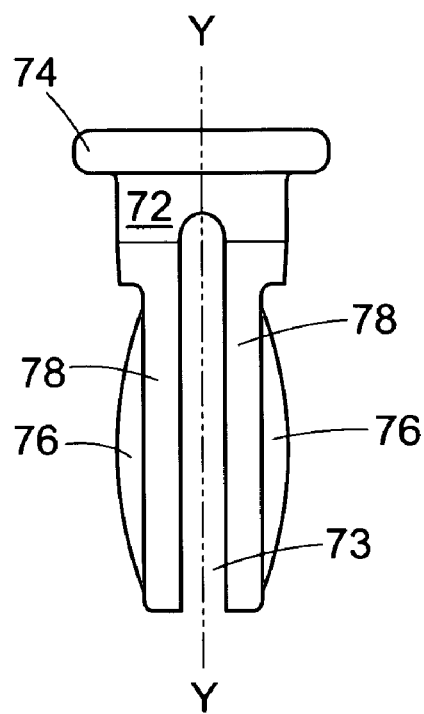
Figure 8B:
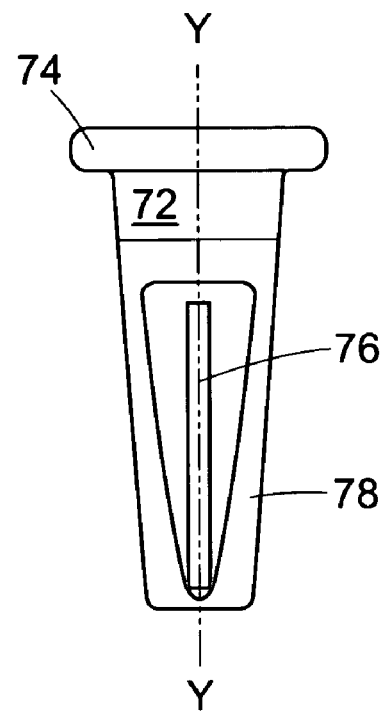
Figure 9A:
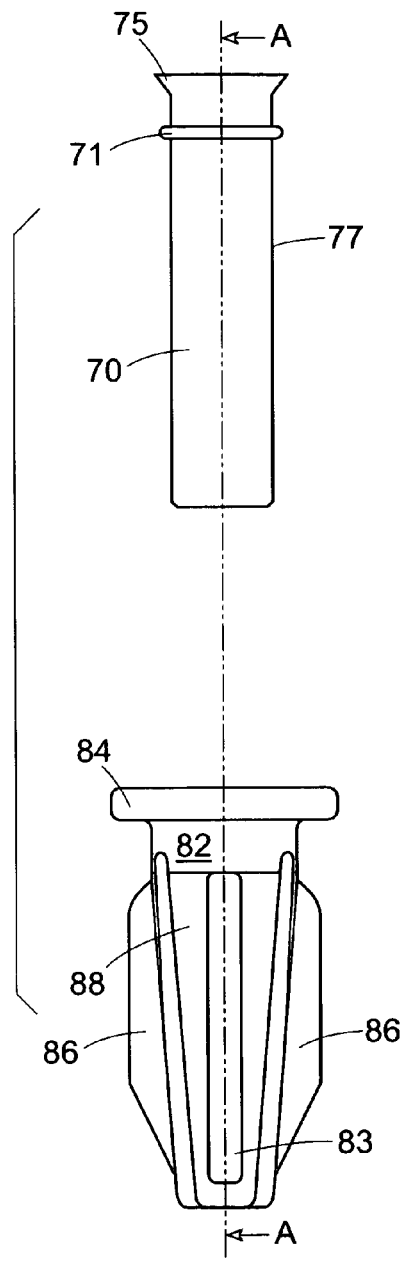
Figure 9B:
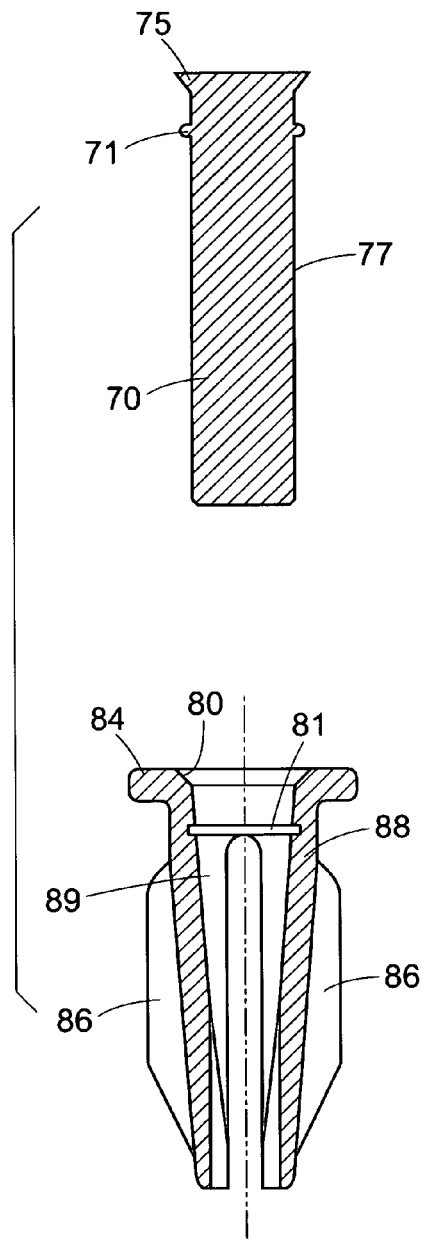
Figure 9C:
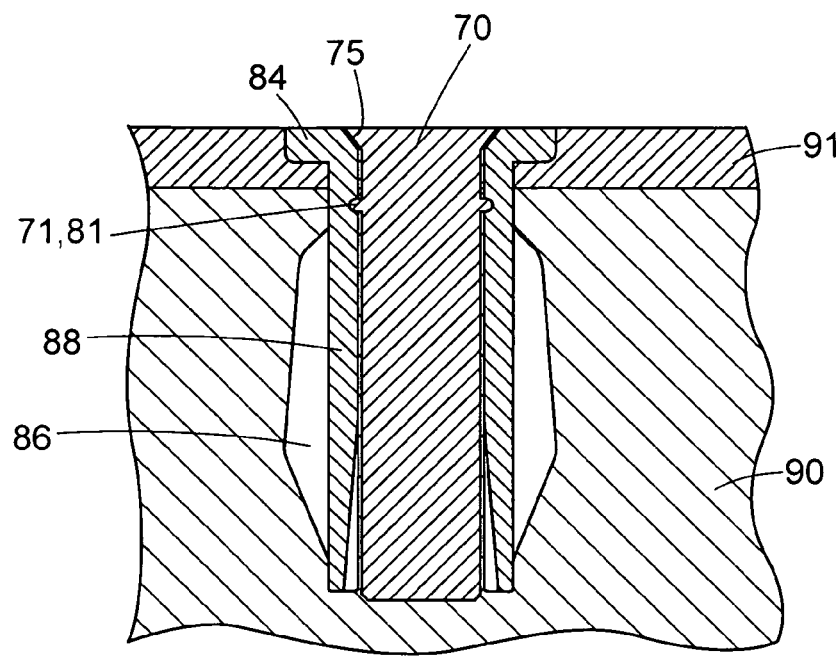
Figure 9D:
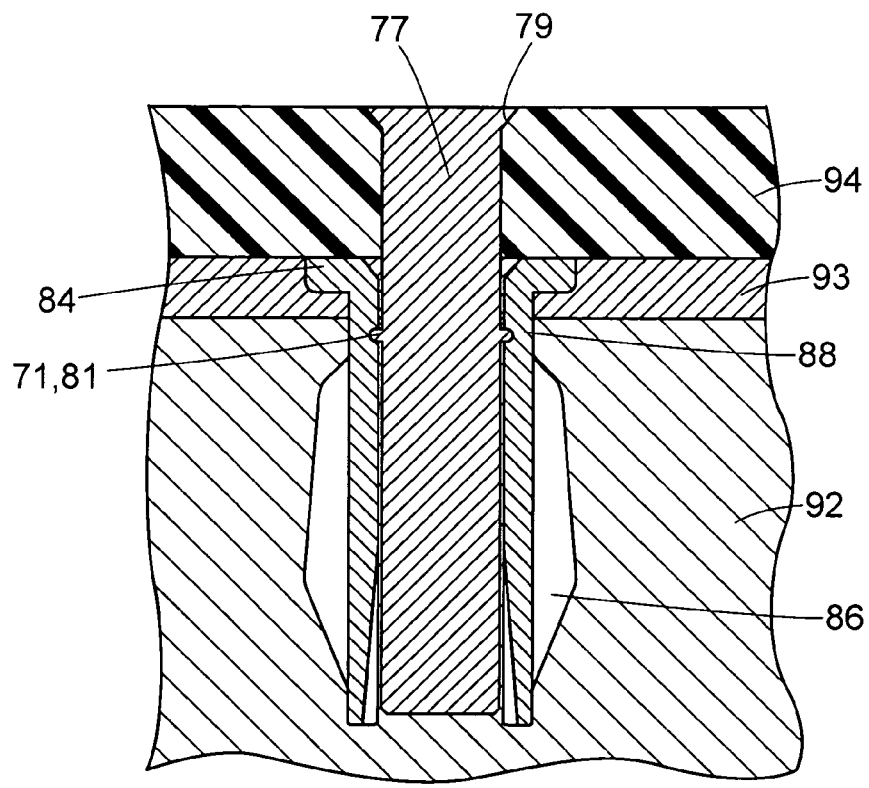
Figure 10:
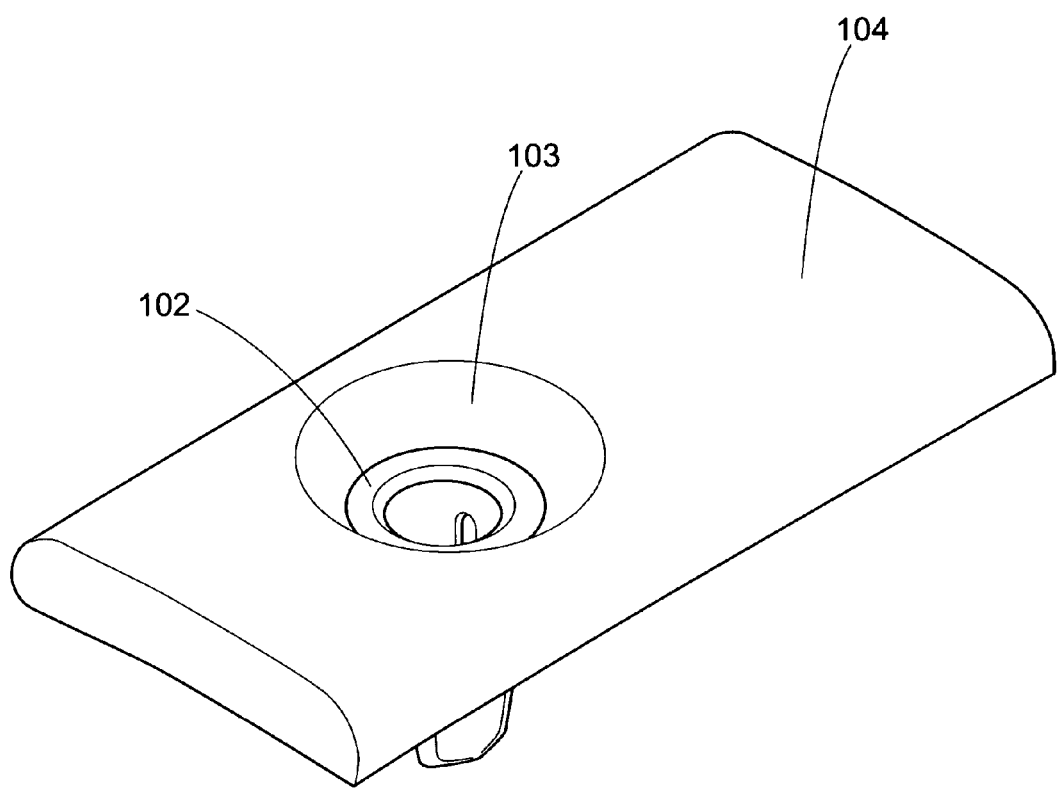
Figure 11A:
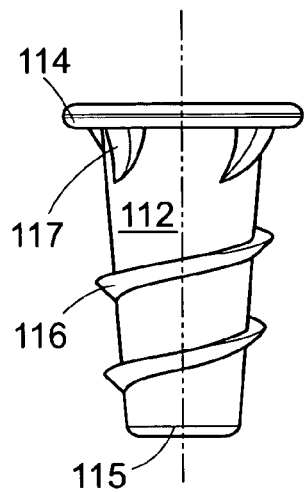
Figure 11B:
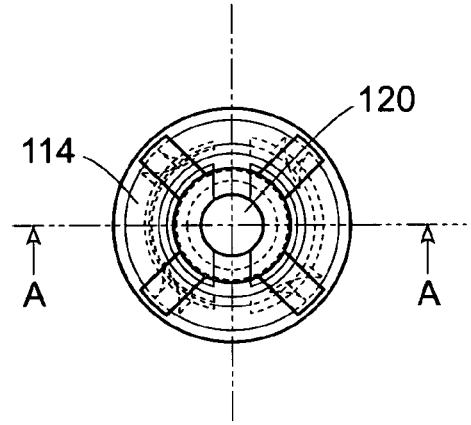
Figure 11C:
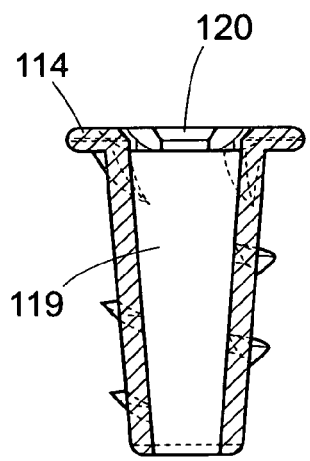
Figure 12A:
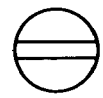
Figure 12B:
Figure 12C:
Figure 12D:
Figure 12E:
Figure 12F:
Figure 12G:
Figure 12H:
Figure 12I:
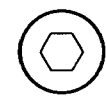
Figure 12J:
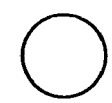
Figure 13A:
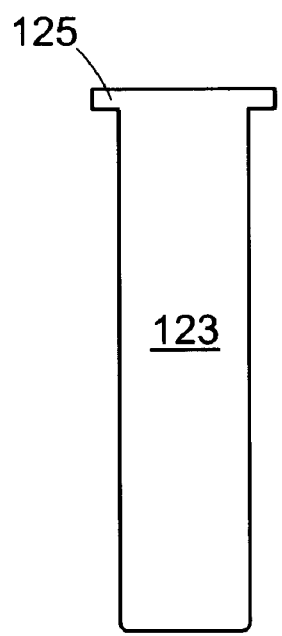
Figure 13B:
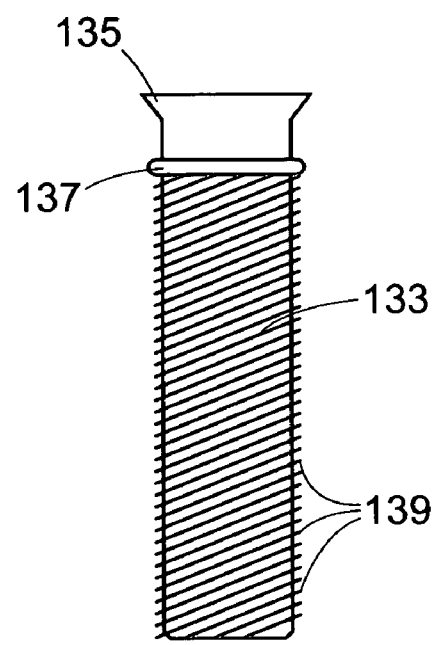

FIG. I-C is a top view of FIG. I-B.

FIG. I-D is a section view of FIG. I-B taken along section line A-A.

FIG. II is an elevation view of a screw/threaded-type fastener of the invention after the screw is inserted into the sleeve.

FIG. III illustrates an elevation of a fastener of the invention implanted in a bone wherein the bone is illustrated partially and in section.

FIG. IV-A is an elevation view of another embodiment of a threaded sleeve of the invention.

FIG. IV-B is a top view of FIG. IV-A.

FIG. IV-C is a section view of FIG. IV-B taken along section line A-A.

FIG. IV-D is a section view of FIG. IV-B taken along section line B-B.

FIG. IV-E is an alternative embodiment of the sleeve of FIG. IV-A having a pointed distal end.

FIG. IV-F is a further alternative embodiment of the sleeve of FIG. IV-A having a bull nose distal end.

FIG. V-A is an elevation view of another embodiment of a threaded sleeve of the invention.

FIG. V-B is a top view of FIG. V-A.

FIG. V-C is a section view of FIG. V-A taken along section line B-B.

FIG. VI-A is an elevation of a wing-type sleeve of the invention.

FIG. VI-B is a top view of FIG. VI-A.

FIG. VI-C is a section view of FIG. VI-A taken along section line A-A.

FIG. VI-D is a section view of FIG. VI-B taken along section line B-B.

FIG. VI-E is an alternative embodiment of the sleeve of FIG. VI-A having sequentially activated wings.

FIG. VII-A is an elevation view of another embodiment of a wing-type sleeve of the invention.

FIG. VII-B is a top view of FIG. VII-A.

FIG. VII-C is a section view of FIG. VII-A taken along section line A-A.

FIG. VII-D is a section view of FIG. VII-B taken along section line B-B.

FIG. VIII-A is an elevation view of still another embodiment of a wing-type sleeve of the invention.

FIG. VIII-B is an elevation view of the sleeve of FIG. VIII-A which has been rotated 90° about the y-y axis.

FIG. IX-A is an elevation view of a pin/wing-type fastener of the invention wherein the sleeve has the same design as the sleeve of FIG. VII except for the added annular recess 81 shown in FIG. IX-B wherein FIG. IX-B is a section view of FIG. IX-A taken along section line A-A.

FIGS. IX-C and IX-D are section views of the sleeve of FIG. IX-A implanted in a bone with a pin set in the sleeve.

FIG. X is a perspective view of a sleeve of the invention installed in a plate, tibial tray or the like.

FIG. XI-A is an elevation view of a sleeve of the invention which is used as a plug.

FIG. XI-B is a top view of FIG. XI-A and FIG. XI-C is a section view taken along section line A-A.

FIGS. XII-A-J illustrate top views of some of the various head configurations for the screws and pins of the invention and some configurations for the flanges.

FIGS. XIII-A and B illustrate in elevation some additional pin and screw embodiments for use with the sleeves of the invention.

DESCRIPTION OF THE PREFERRED EMBODIMENTS

The fasteners of the invention can be made of various biocompatible materials and combinations of biocompatible materials. For example, the sleeve and the corresponding screw or pin of a particular fastener can be made from the same materials or different materials. As another example, the sleeve can be made of different materials so that one portion will be absorbed by the body more quickly than another or one portion will be absorbed and the other will not. Other variations and combinations of materials will be apparent to those having skill in the art. Suitable materials include tissue friendly metals, alloys, synthetic metals, plastics and reinforced plastics which are commonly used in surgical implants of all kinds. Such materials include materials that have sufficient strength to meet the objectives of the invention and that have been approved by the United States Food and Drug Administration (FDA) for surgical implant applications.

Generally speaking, there are three main types of alloys used in orthopedic metals today, titanium alloys, cobalt alloys and stainless steel alloys. An exhaustive list is available on the FDA website which also provides the reference numbers and effective dates of the ASTM or ISO standards for the materials. Some examples include unalloyed and alloyed titanium; molybdenum, chromium, cobalt, tungsten, aluminum, niobium, manganese or vanadium in various combinations as alloys or components of alloys, various stainless steels and other iron alloys; aluminum oxides, zirconium oxides, tantalum and calcium phosphates.

Numerous types of high strength polymers also are employed to make implants and many of these are identified not only on the FDA website mentioned above but also on the ASTM website. Examples of suitable high strength polymers include polyetheretherketone (PEEK), epoxys, polyurethanes, polyesters, polyethylenes, vinyl chlorides, polysulfones, polytetrafluoro-ethylene (PTFE), polycarbonates, polyaryletherketone (PAEK), polyoxymethylene, nylon, carbon fiber polyester, polyetherketoneetherketoneketone (PEKEKK), silicones and the like. When a polymer is used, a small wire or other material can be incorporated in the main body of the base for purposes of x-ray detection.

The foregoing lists of materials may have application in some embodiments of the present invention but not in others as will be apparent to those skilled in the art based on requirements of strength, flexibility, machinability and the like for the particular application. The lists are intended to be illustrative and not exhaustive. Other materials and new materials may be employed based upon the principles of the invention as set forth herein.

For purposes of this specification, the term "high strength polymer(s)" is defined as any tissue-friendly non-bioabsorbable polymer, copolymer, polymer mixture, plastic or polymer alloy having sufficient strength to withstand without failure the torques and stresses that a fastener of the invention would normally be subjected to during surgery or in the body.

Bioabsorbable material can also be used to make all or a portion of one or more of the component parts of the fasteners of the invention and/or the bioabsorbable material can be applied as a partial or complete coating on such component parts.

The term "bioabsorbable material" as used herein includes materials which are partially or completely bioabsorbable in the body.

Suitable bioabsorbable materials include polyglycolide, poly(lactic acid), copolymers of lactic acid and glycolic acid, poly-L-lactide, poly-L-lactate; crystalline plastics such as those disclosed in U.S. Pat. No. 6,632,503 which is incorporated herein by reference; bioabsorbable polymers, copolymers or polymer alloys that are self-reinforced and contain ceramic particles or reinforcement fibers such as those described in U.S. Pat. No. 6,406,498 which is incorporated herein by reference; bioresorbable polymers and blends thereof such as described in U.S. Pat. No. 6,583,232 which is incorporated herein by reference; copolymers of polyethylene glycol and polybutylene terephthalate; and the like. The foregoing list is not intended to be exhaustive. Other bioabsorbable materials can be used based upon the principles of the invention as set forth herein.

Bioactive materials can be admixed with the bioabsorbable materials, impregnated in the bioabsorbable materials and/or coated on the outer surface thereof and/or coated on the base or otherwise provided at the interface of the base with the bioabsorbable material. These materials can include, for example, bioactive ceramic particles, bone chips, polymer chips, capsules or reinforcement fibers and they can contain, for example, antimicrobial fatty acids and related coating materials such as those described in Published U.S. Patent Application No. 2004/0153125 A1; antibiotics and antibacterial compositions; immunostimulating agents; tissue or bone growth enhancers and other active ingredients and pharmaceutical materials known in the art.

The products of the invention can be made by molding, heat shrinking or coating the bioabsorbable material on a base which has been provided with attachment means such as those described in our pending patent application Ser. No. 11/025,213 filed Dec. 29, 2004 which is incorporated herein by reference. Many of the screws, pins and other devices described in our pending patent application Ser. No. 11/025,213 filed Dec. 29, 2004 can also be used in or in combination with the fasteners and/or sleeves of the present invention. When the bioabsorbable material will have functional mechanical properties which are not made from the base material, the bioabsorbable material can be molded onto the base in the desired shape. Alternatively, the bioabsorbable material also can be coated, shrink wrapped or molded onto the base. If necessary, the bioabsorbable material can be machined to the desired shape and/or dimensions.

The fasteners of the invention are implanted in pre-drilled holes in the operating area of a patient. The operating area is usually in bone but it can be in cartilage and bone when a means (e.g., a washer, plate, bracket, wire or equivalent) is used to hold the cartilage down. The pre-drilled hole is sized to accommodate the sleeve so that the fastener will ultimately be implanted in the manner deemed most desirable by the surgeon. It will be understood that sizing the hole means the shape of the hole and any countersinking that may be desired are drilled in a manner that will cause the implanted fastener to be securely affixed in the patient during surgery. In most cases the sleeve will be implanted first. Threaded sleeves are implanted by screwing the sleeve into the pre-drilled hole with a wrench, screwdriver or other driver. Wing-type sleeves are installed by pushing, tapping, impacting or injecting them into place. A pin or screw is then installed in each sleeve at the appropriate time during surgery. In some surgical applications, it may be desirable to have a screw or pin partially inserted into the sleeve before the sleeve is implanted in the patient.

As will be apparent to those skilled in the art, the sizes of the fasteners of the invention can be varied over a broad range to meet their intended applications. The shapes, particularly the outer shapes of the sleeves, can take various forms and the size, lengths, widths and number of the blades, diameters and shapes of the flange, the geometry of the longitudinal slits, etc. can be varied for particular applications within the principles of the invention set forth herein. For example, the lengths of the blades can vary, even on the same sleeve. The flange can be molded or machined together with or separately from the blades. When the flange is made separately, it can be, for example, attached to the blades by heat shrinking, adhesive, tight fit, snap fit or other means known in the mechanical and fastener arts. In some cases it may be desirable for the flange to be made from a different material than the blades, for example, in applications where the flange may need to last longer than the blades or to provide a seat for a screw or pin.

Referring to FIGS. I-A, I-B, I-C, I-D and II, FIG. I-A illustrates in elevation a screw/threaded-type fastener 1 of the invention before the screw 3 is inserted into the sleeve 2. FIG. I-B is an elevation of the sleeve 2 which has been rotated about axis y-y by 90° from FIG. I-A. FIG. I-C is a top view of FIG. I-B and FIG. I-D is a section view of FIG. I-B taken along section line A-A. FIG. II illustrates the fastener 1 shown in FIG. I-A after the screw 3 has been inserted into sleeve 2.

The sleeve 2 is in the shape of a frustum having a proximal end and a distal end and is comprised of a flange 4 at the proximal end. The flange serves to provide a stop for the sleeve to allow it to rest on the cortical surface of the bone or to hold down a plate or other implant device. Various features can be designed into the flange or on the circumference of the flange for driving it into the operating area. This can include hexes, squares, slots, Phillips, spanner holes and the like, either internal or external, sized to mate with appropriate tools for implanting the sleeve into a pre-drilled hole in the operating area.

A foot or web 5 is located at the distal end. The foot or web is an optional feature of the invention and it is useful in applications where increased strength of the sleeve may be necessary during installation of the sleeve and prior to installation of the screw or pin. The foot can be comprised of a thin strip of material at the distal end and can be made of the same or different material as the sleeve. Alternatively, a web of the same or different material as the sleeve can be affixed at the distal end. The foot or web holds together the tips of the blades at the distal end of the sleeve and helps to maintain the integrity of the sleeve and avoid premature breakage when it is implanted.

Threads 6 and anti-rotation wedges 7 are disposed on the outer surface of the frustum, and the frustum generally comprises two blade sections 8. The proximal end has a larger diameter than the distal end.

The screw 3 is comprised of a shank having threads 9 disposed thereon and a head 10.

The longitudinal slit 14 of sleeve 2 extends into an internal tapered bore 12 (see FIG. I-D). The bore becomes narrower as it approaches the distal end and the threads 9, which have diameter larger than the diameter of the bore at the distal end, exert increasing pressure on the sides of the bore 12 as the screw is inserted further into the sleeve through opening 19. The bore as illustrated in FIG. I-A extends through the flange 4 at opening 19 and terminates at the foot or web 5. Two longitudinal slits 14 extend from the outer surface of the frustum to the bore 12, essentially bisecting most of the outer surface of the frustum and thereby forming the blade sections 8. A hexagonal slot 15 is provided so that a hexagonal wrench can be used to screw the sleeve into a bone. It is understood that numerous different kinds of slots, holes or slits can be incorporated into the flange or the outer rim of the flange itself can be shaped (e.g., hexagonally) so that various types of wrenches, screwdrivers and other types of drivers can be used as tools to implant the sleeve into a pre-drilled hole in the operating area of the patient. It is also understood that the sleeve can have more than two blades and, in fact, can have several blades as may be appropriate or necessary for particular applications. The blades can be straight or tapered and can be of various shapes and sizes, even on the same sleeve.

Threads 16 mate with the threads 9 of screw 3. In alternative embodiments, self-tapping screws can be used, particularly when the sleeve is made from a softer material than the screw. When self-tapping screws are used it is not necessary to have threads such as threads 16 in the sleeve. It should be noted that any sleeve of the invention can be designed to work with a screw or a pin to make fasteners for particular applications as will be apparent to those skilled in the art. The opening in the flange which receives the screw or pin accordingly can be straight or tapered or threaded or a combination of any or all. As described above, the sleeve can be supplied with a mated screw, a self-tapping screw, a pin, a rod or any other device which can be affixed in the sleeve.

When screw 3 is inserted into sleeve 2, the foot or web 5 is caused to break, as illustrated in FIG. II, by the pressure exerted by the screw on the sides of the bore 12. The broken foot or web 5 leaves a gap 11 and the blade sections 8 are caused to move laterally in the directions x-x, thereby expanding the sleeve. Of course, threads 6 are also caused to move in the same lateral directions. This expansion or lateral movement secures and stabilizes the sleeve in the bone and allows the bone to grow into the space occupied by the fastener as the healing process progresses.

FIG. III illustrates a screw/threaded-type fastener of the invention implanted in a bone 20. The bone 20 is a portion of a bone and is illustrated in section whereas the fastener is illustrated in elevation. The bone 20 is comprised of a cortical portion 21 and a cancellous portion 22. The head 10 of the screw is provided with a transverse bore 13 which extends across the diameter of the head. The transverse bore 13 can accommodate sutures and the fastener accordingly can be used as a suture anchor or a bone anchor.

As we have described in the foregoing discussion of FIG. II, the blades 8 and threads 6 have been moved laterally due to pressure exerted by the screw. This lateral movement into the cancellous portion 22 accordingly exerts pressure on the bone thereby securing the fastener firmly in place and preventing rotation or other undesired movement of the sleeve during the installation therein of a screw or a pin and following the installation of the screw or pin. A typical example of an application for the fastener of FIG. III would be to replace a conventional suture anchor that was over-tightened, causing the hole in the bone to be stripped out. The replacement suture anchor could be implanted at the same location as the stripped out hole in the bone, the hole being accommodated to fit the replacement, and a second hole would not have to be drilled at another location on the bone.

Referring to FIGS. IV-A, B, C and D, FIG. IV-A illustrates in elevation a threaded sleeve 32 in the shape of a frustum having a proximal end and a distal end. Flange 34 is affixed at the proximal end and a foot or web 35 at the distal end. Threads 36 are disposed on the outer surface of the frustum. The anti-rotation wedges 37 are somewhat curved or angled generally in the direction of the threads and generally extend downwardly from the flange along the outer surface of the frustum. The anti-rotation wedges can be straight, angled or curved as a matter of design choice that will be apparent to those skilled in the art based upon the disclosures herein. The frustum has blade sections 38. Longitudinal slits 33 extend into internal tapered bore 39. In the top view, FIG. IV-B, slots 31 are provided for a cruiform screwdriver which is used to insert the sleeve into a pre-drilled hole in the patient's bone. Referring to FIGS. IV-C and D, a tapered recess 30 is provided in the flange 34 so that a screw or pin with a tapered head can be seated in a position flush with the top surface of the flange. The internal tapered bore 39 is illustrated in FIG. IV-D and the bore is sized so that the diameter d near the distal end is less than the diameter of the screw or pin which is inserted into the proximal end of the sleeve through opening 29. Accordingly, when the screw or pin is inserted, the foot or web 35 is caused to break and the blades 38 are pushed laterally outward thereby affixing the sleeve more securely in the bone.

FIG. IV-E illustrates an alternative embodiment of the sleeve of FIG. IV-A having a pointed distal end 23 and a slit 24. The slit permits the blades to move apart laterally when a screw or pin is installed in the sleeve. FIG. IV-F illustrates still another embodiment with a bull nose distal end 25 and a slit 26. The pointed distal end and the bull nose distal end, each with a slit as illustrated (and the slit can be a very thin slit such as a hairline slit) can be provided as an element of the design of any of the various sleeves of the invention. Either design is particularly useful in applications where possible breakage of the bone may be caused by installation of the sleeve.

Turning to FIGS. V-A, B and C, FIG. V-A illustrates in elevation a threaded sleeve 2 having threads 46 positioned near the flange 44 so that they primarily engage the outside cortical shell of the bone. The flange 44 is also tapered so that its upper surface can be flush with the surface of the bone or a plate when it mates with a pre-drilled countersink at the outer edge of the pre-drilled hole in the bone or plate. In most cases countersinks are made in plates rather than in bone but in some operations, for example in the knee, a countersink in the bone may be desirable. The sleeve has three blades 48 and an internal tapered bore 49. The longitudinal slits 43 extend all the way to a web 45 at the distal end. After the sleeve is installed, a screw or pin is inserted into opening 28 and tapered portion 40 allows the screw or pin to be installed so that the top surface of the screw or pin is flush with the top surface of the sleeve and the bone.

FIGS. VI-A, B, C and D illustrate a wing-type sleeve 52 having wings 56 longitudinally disposed thereon. An elevation of sleeve 52 is illustrated in FIG. VI-A with a flange 54 at the proximal end and a foot or web 55 at the distal end. When a pin or screw is inserted into opening 27, it causes the wings 56 to be actuated (i.e., pushed outwardly in a generally lateral direction). If desired, the screw or pin can be sized so that it does not reach the foot or web 55 when fully inserted into the sleeve, in which case the foot or web will not break but will remain closed. Alternatively, a longer screw or pin can be used which will break the foot or web 55 when fully inserted thereby also causing blades 58 to be actuated (i.e., pushed outwardly in a generally lateral direction).

FIG. VI-E is an alternative embodiment of sleeve 52, illustrated in the same section view as shown in FIG. VI-C. In this embodiment, when a screw or pin is inserted into opening 27, wing 56a is actuated before wing 56 is actuated because the screw or pin will reach wing 56a before it reaches wing 56. This sequential actuation is particularly useful to prevent rotation of the sleeve when a screw is inserted into opening 27 and when a lot of pressure is being exerted on the screw which could otherwise cause rotation of the sleeve. Only two wings are illustrated in this embodiment but more than two could be used with each wing being sequentially actuated or with pairs or groups of wings being simultaneously actuated followed by individual or multiple other wings being sequentially or simultaneously actuated. Another example of sequential actuation is described in the foregoing paragraph discussing FIGS. VI-A, B, C and D wherein the wings 56 are actuated followed by actuation of blades 58.

Another embodiment of a wing-type sleeve 62 is illustrated in FIGS. VII-A, B, C and D. FIG. VII-A illustrates the sleeve in an elevation view and FIG. VII-B is a top view of FIG. VII-A. FIG. VII-C is a section view taken along section line A-A and FIG. VII-D is a section view taken along section line B-B. The sleeve has three blades 68 each having a wing 66 affixed and longitudinally disposed thereon. Longitudinal slits 63 open to an internal tapered bore 69. The bore extends through the flange 64 at opening 26 and a tapered portion 60 allows a screw or pin to be installed so that the top surface of the screw or pin is flush with the top surface of the sleeve. The top surface of the sleeve can also be made flush with the top surface of a bone or plate or other implant device in which it is installed by preparing the bone or plate or other implant device with a countersink which is sized to accommodate the flange 64.

FIGS. VIII-A and VIII-B illustrate still another embodiment of a wing-type sleeve of the invention. Both figures are elevation views with FIG. VIII-B illustrating the sleeve of FIG. VIII-A after it has been rotated 90° about the y-y axis. The sleeve 72 is provided with a flange 74, two blades 78, two wings 76 and a longitudinal slit 73. It should be noted that this sleeve does not have a foot or a web. And when such sleeves are installed in a pre-drilled hole, the hole may be sized to cause the blades to move toward one another at the distal end of the sleeve. This results in more deflection of the blades into the bone and a tighter fit when a screw or pin is inserted into the sleeve.

FIGS. IX-A and IX-B illustrate a sleeve of the type shown in FIG. VII except that an annular recess 81 is provided to receive an optional annular ring 71 disposed in an annular groove on the shank 77 of pin 70. When the pin is installed in the sleeve with a slight tap such as from a hammer, the annular ring 71 is snap fit into the annular recess 81 thereby holding the pin firmly in place. Head 75 of the pin 70 is seated in tapered portion 80 of the flange 84 when the pin is installed in the sleeve. Longitudinal slits 83 extend into the tapered bore 89.

Referring to FIG. IX-C, after the sleeve is installed in a bone, the top surface of the pin is flush with the top surface of the sleeve and a countersink recess can be made in the cortical portion 91 of the bone so that the entire fastener is flush with the top surface of the bone. The installation of the pin 70 into the sleeve 82 causes the blades 88 and the wings 86 to move laterally into the cancellous portion 90 of the bone thereby firmly affixing the fastener in the bone. In the figure, the head of the pin is flush with the top surface of the flange and the cortical portion. Of course, other head designs which are not flush can be used.

FIG. IX-D illustrates a variation of FIG. IX-C wherein a longer pin 77 is used to affix a plate 94 to a bone. The cortical portion of the bone 93 is drilled to accommodate the flange 84 and the optional annular ring 71 is located on the pin 77 at a certain measured distance from head 79 so that the top surface of head 79 will be flush with the top surface of the plate 94 when the ring 71 is snap fit into sleeve 82 at annular recess 81. The sleeve is affixed in the bone in the same manner as described in respect of FIG. IX-C wherein the blades 88 and the wings 86 are laterally extended into the cancellous portion 92 of the bone.

FIG. X is a perspective view of a sleeve 102 installed in a countersink 103 in a plate or tibial tray 104. Comparing FIG. IX-D, this is a different way of using the fastener of the invention in combination with a plate because in this case the sleeve is countersunk in the plate and affixed in the bone. In FIG. IX-D the sleeve is fixed only in the bone and the pin secures the plate.

FIGS. XI-A, B and C illustrate sleeve 112 having a flange 114 at the proximal end, a foot or web 115 at the distal end, threads 116 and anti-rotation wedges 117. Opening 120 provides access to cavity 119. There are no longitudinal slits or blades as required of the other sleeves of the invention. Sleeve 112 can be used as a plug and the cavity can optionally be filled with any form or combination of bone, coral, PEEK chips, allograph, ceramics, bone wax, medications such as antibiotics, bioactive materials, antibacterial compositions, immunostimulating agents, tissue or bone growth enhancers and other active and inactive ingredients and pharmaceutical materials known in the art. A suitable screw, pin or plug is used to close opening 120 after the sleeve is implanted and the cavity has been optionally filled with a foregoing material. This sleeve can have any desired shape or size as with the other sleeves of the invention. The sleeve optionally can be made from a bioabsorbable material which will gradually dissolve and cause the contents to be released over time. The other sleeves of the invention which have longitudinal slits and blades can be used in the same manner as sleeve 112 wherein the slits will allow for more rapid release of any active materials that may be filled into the internal bore. The slits also permit faster bone growth. When a sleeve of the invention is used as a plug as described herein it is normally used to fill a hole created by a previous procedure such as the removal of implants of various kinds such as screws, halos and the like. The plugs can stop bleeding, prevent infection, enhance bone growth and perform various other beneficial functions.

FIG. XII-A-J illustrates top views of some of the head design types for screws and pins that can be used in the invention and some of the design types for the flanges. These illustrations are not intended to include all of the possible designs and others can be used as will be apparent to those skilled in the art. All of the illustrated designs can be used for flanges or pin heads and FIGS. XII-A-I can be used for screws. It will be understood by those having skill in the art based upon the disclosures herein that that when any of the designs are used for a flange they will also include an opening for a screw or a pin. An example of such an opening being the opening 19 in a flange having an internal hex as illustrated in FIG. IC. FIG. XII-A illustrates a standard slot. FIG. XII-B can be a Philips or a cruiform. FIG. XII-C is a spanner and D is a torq. FIG. XII-E is an Allen, F is a square head and G is an external hex. FIG. XII-H is a new design, I is an internal hex and J is a pin head or flange.

FIG. XIII-A illustrates in elevation a pin 123 with head 126 and FIG. XIII-B illustrates in elevation a screw 133 with a head 135, a retaining ring 137 disposed in an annular ring on the shank and threads 139 disposed on said shank. These are intended to show some alternative embodiments to those screws and pins already illustrated. Variations thereon will be apparent to those skilled in the art. Either the pin 123 or the screw 133 could be used, for example, with the sleeve of FIGS. IX-A and B. The retaining ring 137 illustrated on the screw 133 prevents rotation and loosening of the screw after it is installed in the sleeve, but the retaining ring does not prevent the intentional removal of the screw by a surgeon.

The invention claimed is:

1. A biocompatible sleeve component of a surgical fastener having a proximal end and a distal end and an outer surface disposed between the proximal end and the distal end, the proximal end having a flange thereon,
   the flange being adapted to rest on the cortical surface of a bone or to hold down on the cortical surface of a bone a plate, cartilage, a tendon or other implant,
   a bore adapted to receive a screw or a pin and extending through the flange toward the distal end and terminating at or before the distal end,
   at least two longitudinal slits extending from the bore through the outer surface, said slits defining, in the sleeve, blade sections extending from one slit to another,
   the outer surface having threads disposed thereon or one or more wings longitudinally disposed thereon,
   wherein the blade sections are caused to move laterally in a direction away from the bore when a screw or a pin is inserted into the bore.

2. The biocompatible sleeve of claim 1 further comprising one or more anti-rotation wedges extending from the flange along the outer surface toward the distal end.

3. The biocompatible sleeve of claim 1 wherein the bore terminates at a foot or web at the distal end wherein the foot or web is broken by the insertion of a screw or pin into the bore thereby allowing the blade sections to move laterally.

4. The biocompatible sleeve of claim 1 wherein the flange is adapted to receive a tool for inserting the sleeve into an operating area of a patient.

5. The biocompatible sleeve of claim 1 wherein the bore is tapered so that the cross-section of the bore at the distal end is smaller than the cross-section of the bore at the proximal end.

6. The biocompatible sleeve of claim 1 wherein the bore is at least partially threaded to receive a screw.

7. The biocompatible sleeve of claim 1 wherein the outer surface is in the shape of a cylinder or a frustum, the frustum having a larger diameter at the proximal end than at the distal end.

8. The biocompatible sleeve of claim 1 having two or more than two blade sections.

9. The biocompatible sleeve of claim 1 wherein the outer surface is sufficiently partially threaded to secure the sleeve in the cortical shell of a bone of a patient.

10. The biocompatible sleeve of claim 1 wherein one wing is disposed on the outer surface of each blade section.

11. The biocompatible sleeve of claim 1 wherein at least one first blade section is caused to move laterally in a direction away from the bore when a screw or pin is inserted into the bore and before at least one other blade section is caused to move laterally in a direction away from the bore when a screw or pin is inserted into the bore.

12. A method of implanting in an operating area of a patient the surgical fastener of claim 11 comprising drilling the operating area to make a hole that will accommodate the sleeve, inserting the sleeve into the hole, inserting a screw or pin into the bore to cause the at least one first blade section to move laterally away from the bore, further inserting the screw or pin into the bore to cause the at least one other blade section to move laterally away from the bore, thereby securing the fastener in the operating area.

13. The biocompatible sleeve of claim 1 wherein the distal end is in the shape of a point or a bull nose.

14. A combination of the surgical fastener of claim 1 and an operating area of a patient wherein the surgical fastener is implanted in the operating area.

15. The combination of claim 14 wherein the operating area is selected from the group consisting of a bone, cartilage and both bone and cartilage.

16. A method of implanting in an operating area of a patient the sleeve of claim 1 comprising drilling the operating area to make a hole that will accommodate the sleeve and inserting the sleeve into the hole.

17. The method of claim 16 wherein the operating area is selected from the group consisting of a bone, cartilage and both bone and cartilage.

18. The method of claim 16 wherein drilling the operating area to make a hole further comprises countersinking.

19. A surgical fastener comprised of biocompatible material and further comprising:
   a sleeve having a proximal end and a distal end and an outer surface disposed between the proximal end and the distal end, the proximal end having a flange thereon,
   the flange being adapted to rest on the cortical surface of a bone or to hold down on the cortical surface of a bone a plate, cartilage, a tendon or other implant,
   a bore extending through the flange toward the distal end and terminating at or before the distal end,
   at least two longitudinal slits extending from the bore through the outer surface, said slits defining, in the sleeve, blade sections extending from one slit to another, the outer surface of the sleeve having threads disposed thereon or one or more wings longitudinally disposed thereon,
   a screw which can be threaded into the bore or a pin which can be inserted into the bore from the proximal end toward the distal end causing the blade sections to move in a direction laterally away from the bore.

20. The surgical fastener of claim 19 wherein the screw or pin comprises a head and a shank and a retaining ring disposed in an annular groove on the shank, and the sleeve comprises an annular recess in the bore to receive the retaining ring.

21. A combination of the surgical fastener of claim 19 and an operating area of a patient wherein the surgical fastener is implanted in the operating area.

22. A method of implanting in an operating area of a patient the surgical fastener of claim 19 comprising drilling the operating area to make a hole that will accommodate the sleeve, inserting the sleeve into the hole, inserting a screw or pin into the bore to cause the blade sections to move laterally away from the bore, thereby securing the fastener in the operating area.

23. A combination of a surgical fastener of claim 19, an operating area of a patient and a medical implant device wherein the surgical fastener is implanted in the operating area and secures the medical implant device to the operating area.

24. The surgical fastener of claim 19 comprising two or more wings wherein at least one wing is caused to move in a direction laterally away from the bone before at least one other wing is caused to move in a direction laterally away from the bone.

25. A surgical fastener comprised of biocompatible material and further comprising:
   a sleeve having a portion of its outer surface in the shape of a frustum, the frustum having a proximal end and a distal end, each end having a diameter wherein the diameter at the proximal end is larger than the diameter at the distal end, a flange affixed at the proximal end, the flange being adapted to rest on the cortical surface of a bone or to hold down on the cortical surface of a bone a plate, cartilage, a tendon or other implant,
   a bore extending through the flange and the frustum towards the distal end and terminating at a foot or web comprising the distal end, at least two longitudinal slits extending from the bore through the outer surface of the frustum, said slits defining, in the frustum, blade sections extending from one slit to another, the outer surface of the frustum being threaded or having one or more wings longitudinally disposed thereon,
   a screw which can be threaded into the bore or a pin which can be inserted into the bore from the proximal end causing the foot or web to break and the blade sections to move in a direction laterally away from the bore.

26. A combination of the surgical fastener of claim 25 and an operating area of a patient wherein the surgical fastener is implanted in the operating area.

27. A method of implanting in an operating area of a patient the surgical fastener of claim 25 comprising drilling the operating area to make a hole that will accommodate the sleeve, inserting the sleeve into the hole, inserting a screw or pin into the bore to cause the blade sections to move laterally away from the bore, thereby securing the fastener in the operating area.

28. A biocompatible sleeve component of a surgical fastener having a proximal end and a distal end and an outer surface disposed between the proximal end and the distal end, the proximal end having a flange thereon,
   the flange being adapted to rest on the cortical surface of a bone or to hold down on the cortical surface of a bone a plate, cartilage, a tendon or other implant,
   the outer surface having threads disposed thereon or one or more wings longitudinally disposed thereon,
   a bore extending through the flange into a cavity,
   a material optionally disposed in the cavity and selected from the group consisting of active and inactive ingredients and pharmaceutical materials and combinations thereof;
   a plug disposed in the bore.

* * * * *